(12) United States Patent
Hong

(10) Patent No.: US 8,221,017 B2
(45) Date of Patent: Jul. 17, 2012

(54) FLUID APPLICATOR

(76) Inventor: Kun-Liang Hong, Chungho (TW)

(*) Notice: Subject to any disclaimer, the term of this patent is extended or adjusted under 35 U.S.C. 154(b) by 623 days.

(21) Appl. No.: 12/385,928

(22) Filed: Apr. 24, 2009

(65) Prior Publication Data

US 2010/0272497 A1    Oct. 28, 2010

(51) Int. Cl.
B43K 8/06    (2006.01)
(52) U.S. Cl. .................. 401/198; 401/132; 222/187
(58) Field of Classification Search .............. 401/198,
401/205, 141, 142, 132, 133, 187, 188 R,
401/189; 604/3; 222/187, 188
See application file for complete search history.

(56) References Cited

U.S. PATENT DOCUMENTS 3,495,917 A * 2/1970 Truhan ................... 401/132
3,958,571 A * 5/1976 Bennington ............... 604/3
5,702,035 A * 12/1997 Tsao ...................... 222/187
6,129,894 A * 10/2000 Rabenecker et al. ........ 422/430

* cited by examiner

Primary Examiner — David J. Walczak
Assistant Examiner — Jennifer C Chiang
(74) Attorney, Agent, or Firm — Rosenberg, Klein & Lee

(57) ABSTRACT

A fluid applicator includes a tubular container having a top open end and a bottom open end, a floating stopper mounted in the tubular container for sealing the bottom open end of the tubular container, a fluid filled in between the top open end and bottom open end of the tubular container, and a plug for closing the top open end of the tubular container. When the plug is opened from the top open end of the tubular container for allow the atmospheric pressure to enter the tubular container, the floating stopper is forced to adhere to the peripheral wall of the tubular container for allowing the fluid to flow out of the fluid container. When the plug seals the top open end of the tubular container, the atmospheric pressure is prohibited from entering the tubular container, and the floating stopper stops the bottom open end of the tubular container again.

16 Claims, 3 Drawing Sheets

FLUID APPLICATOR

BACKGROUND OF THE INVENTION

1. Field of the Invention

The present invention relates to a fluid applicator for holding a fluid for application and more particularly, to such a fluid applicator, which is convenient for carrying and application.

2. Description of the Related Art

Many fluid applicators are commercially available. A known fluid applicator has a tubular container with a breakable portion. When breaking the breakable portion, the atmospheric pressure enters the tubular container, enabling the contained fluid to flow out of the other end of the tubular container for application.

There is known another prior art design of fluid applicator having an applicator stick shaped like a cotton swab and retained in an enclosed tubular fluid container. The tubular fluid container has a breakable portion. During application, break the breakable portion to let the applicator stick be exposed to the outside for applying the contained fluid to the desired surface area.

The aforesaid two prior art designs are not convenient for use. When breaking the breakable portion, the contained fluid may splash over the surroundings. Further, the design of the breakable portion relatively increases the length of the fluid applicator.

SUMMARY OF THE INVENTION

The present invention has been accomplished to provide a fluid applicator that eliminates the aforesaid drawbacks.

A fluid applicator in accordance with the present invention comprises a tubular container having a top open end and a bottom open end, a floating stopper mounted in the tubular container for sealing the bottom open end of the tubular container, a fluid filled in between the top open end and bottom open end of the tubular container, and a plug for closing the top open end of the tubular container. When the plug is opened from the top open end of the tubular container for allow the atmospheric pressure to enter the tubular container, the floating stopper is forced to adhere to the peripheral wall of the tubular container for allowing the fluid to flow out of the fluid container. When the plug seals the top open end of the tubular container, the atmospheric pressure is prohibited from entering the tubular container, and the floating stopper stops the bottom open end of the tubular container again.

Further, the plug has a plug base that can be press-fitted into the top open end of the tubular container to seal the passage, and a split bolt extended from the bottom end of the plug base and slidably coupled to the top open end of the tubular container to prohibit disconnection of the plug from the tubular container and for allowing the plug base is set into the top open end of the tubular container or moved away from the top open end of the tubular container.

DETAILED DESCRIPTION OF THE PREFERRED EMBODIMENT

Figure 1:
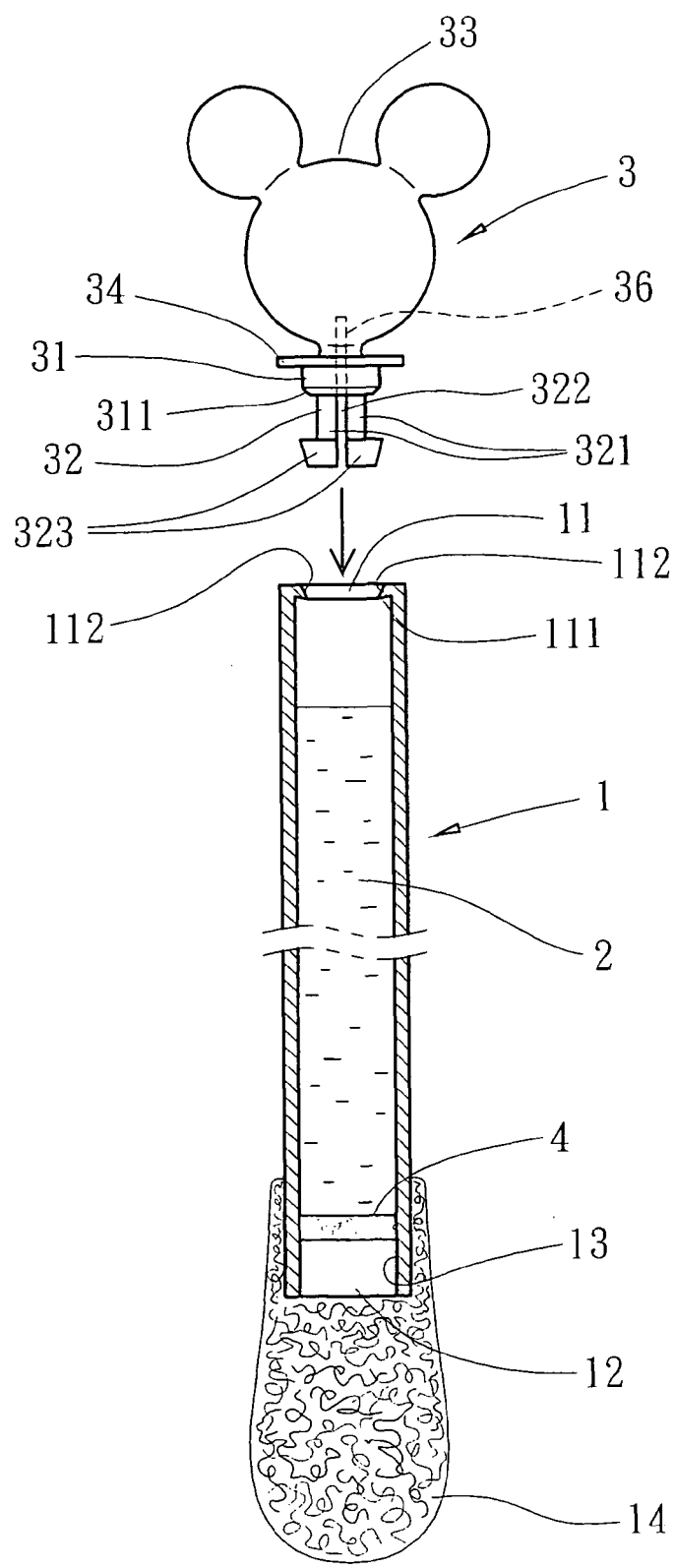
FIG. 1 is a schematic sectional exploded view of a fluid applicator in accordance with a first embodiment of the present invention.
Figure 3:
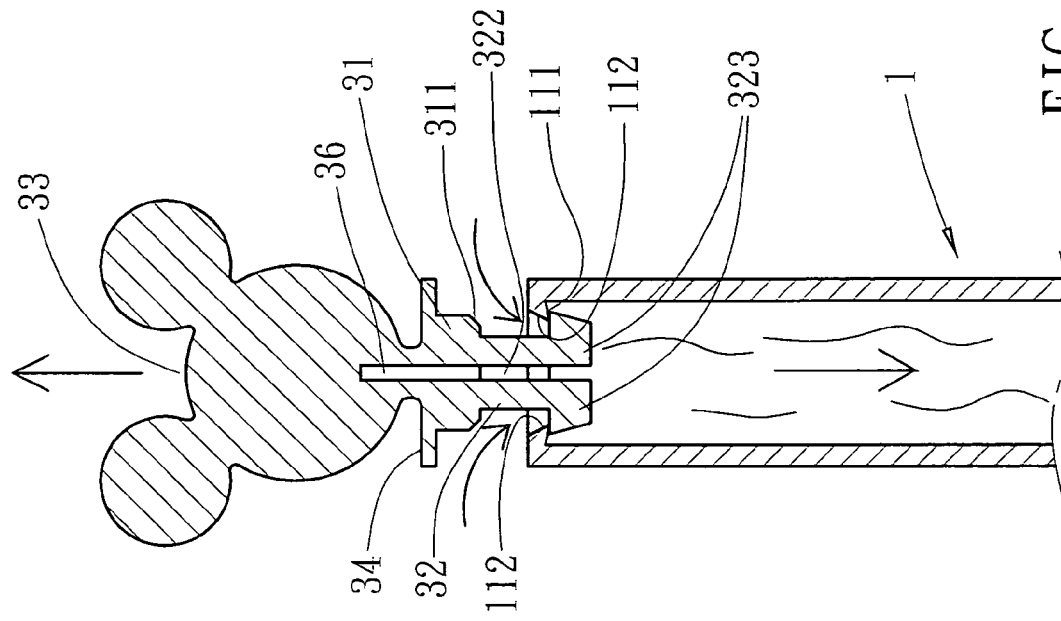
FIG. 3 corresponds to FIG. 2, showing the plug base of the plug press-fitted disengaged from the tapered inner diameter of the inside annular flange of the fluid container and the top open end of the tubular container opened.
Figure 2:
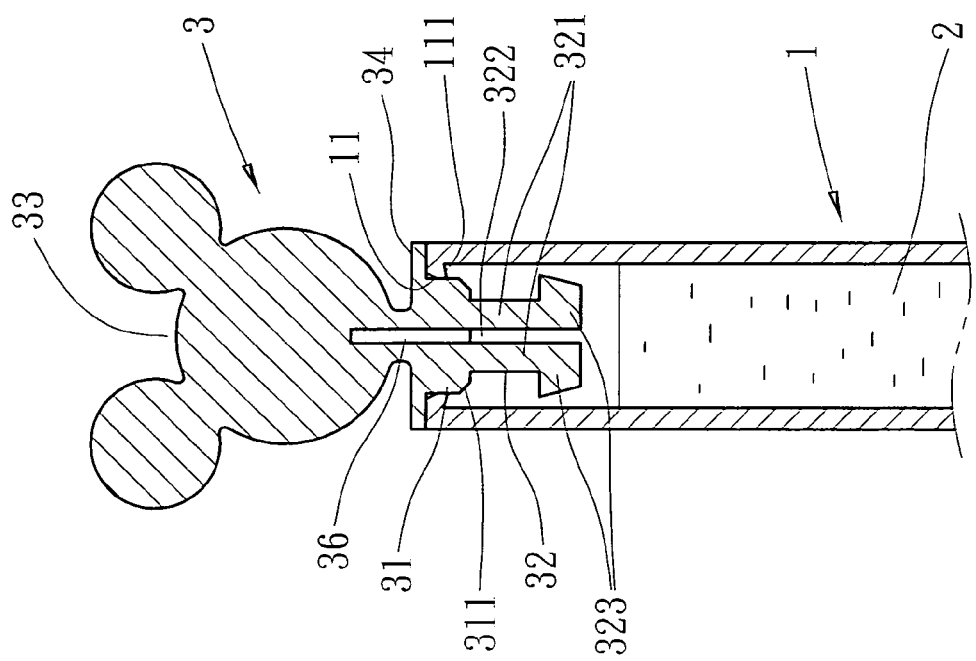
FIG. 2 is a sectional view of a part of the fluid applicator in accordance with the first embodiment of the present invention, showing the plug base of the plug press-fitted into the tapered inner diameter of the inside annular flange of the fluid container and the shoulder of the plug stopped at the top open end of the tubular container.

Referring to FIGS. 1~3, a fluid applicator in accordance with a first embodiment of the present invention is shown comprising a tubular container 1, a plug 3 and a floating stopper 4.

The tubular container 1 has a top open end 11, a bottom open end 12 opposite to the top open end 11, and an inside annular flange 111 radially inwardly protruded from the inside wall 13 at the top open end 11.

The plug 3 is coupled to the tubular container 1 and movable axially relative to the tubular container 1 to close/open the top open end 11. The plug 3 has a plug base 31 that fits the tapered inner diameter 112 of the inside annular flange 111 tightly to seal the passage of the top open end 11, a split coupling bolt 32 axially forwardly extended from one end, namely, the bottom end of the plug base 31 and slidably coupled to the inside annular flange 111, a shoulder 34 that is located on the other end, namely, the top end of the plug base 31 and has a diameter greater than the outer diameter of the tubular container 1 and can be stopped outside the top open end 11 of the tubular container 1, a head 33 formed integrally with the top side of the shoulder 34 opposite to the plug base 31 and made in any of a variety of shapes, for example, the shape of a cartoon figure, and a blind hole 36 axially extending through the plug base 31, the split coupling bolt 32 and the shoulder 34 into the inside of the head 33. The split coupling bolt 32 has a plurality of bolt elements 321 and a plurality of longitudinal crevices 322 that separate the bolt elements 321. Each bolt element 321 has the free end terminating in a hooked portion 323.

The floating stopper 4 is prepared from a liquid material having a high molecular weight that is not volatile under room temperature, and inserted into the tubular container 1 for sealing the bottom open end 12.

Further, a fluid, for example, a liquid medicine, alcohol or perfume 2 is contained in the tubular container 1.

When the plug base 31 of the plug 3 is press-fitted into the tapered inner diameter 112 of the inside annular flange 111 to close the top open end 11 of the tubular container 1, the atmospheric pressure is prohibited from entering the tubular container 1, and the floating stopper 4 is functioning to seal the bottom open end 12. On the contrary, when pulling the plug 3 outwards to disengage the plug base 31 from the inside annular flange 111, the top open end 11 of the tubular container 1 is opened for allowing entering of the atmospheric pressure into the inside of the tubular container 1 to force the fluid 2 against the floating stopper 4, thus the floating stopper 4 is adhered to the inside wall 13 of the tubular container 1 for allowing the fluid 2 to flow out of the bottom open end 12 of the tubular container 1 for application.

Further, an absorptive applicator tip 14 is fastened to the bottom open end 12 of the tubular container 1 for absorbing the fluid 2 for application.

Further, the plug base 31 of the plug 3 has a chamfered bottom edge 311 that facilitates press-fitting of the plug base 31 into the tapered inner diameter 112 of the inside annular flange 111 of the tubular container 1.

Figure 4:
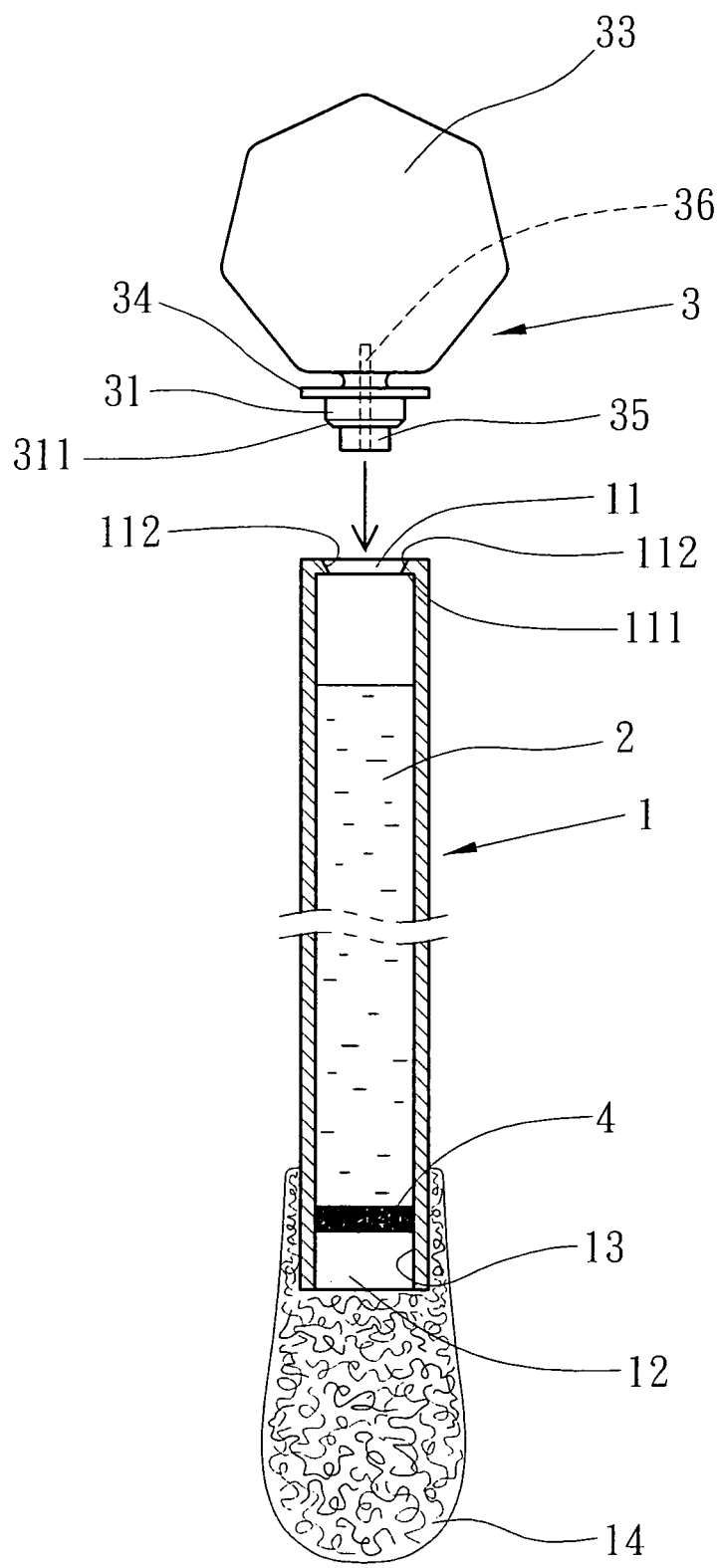
FIG. 4 is a schematic sectional exploded view of a fluid applicator in accordance with a second embodiment of the present invention.

FIG. 4 shows a fluid applicator in accordance with a second embodiment of the present invention. This embodiment is substantially similar to the aforesaid first embodiment with the exception of the design of the plug 3. According to this second embodiment, the plug 3 eliminates the aforesaid split coupling bolt 32, and has a stub rod 35 axially forwardly extended from the bottom end of the plug base 31.

A prototype of fluid applicator has been constructed with the features of FIGS. 1~4. The fluid applicator functions smoothly to provide all of the features disclosed earlier.

Although particular embodiments of the invention have been described in detail for purposes of illustration, various modifications and enhancements may be made without departing from the spirit and scope of the invention. Accordingly, the invention is not to be limited except as by the appended claims.

What the invention claimed is:

1. A fluid applicator, comprising:
    a tubular container having a top open end and a bottom open end opposite to said top open end;
    a floating stopper mounted in said tubular container and adapted to seal said bottom open end;
    a fluid filled in said tubular container in between said top open end and said bottom open end; and
    a plug for closing the top open end of said tubular container; and
    wherein when said plug is opened from said top open end of said tubular container for allowing the atmospheric pressure to enter said top open end, said floating stopper is forced to adhere to the peripheral wall of said tubular container for allowing said fluid to flow out of said bottom open end; when said plug seals said top open end of said tubular container, the atmospheric pressure is prohibited from entering said top open end, and said floating stopper stops said bottom open end again, said tubular container has an inside annular flange located on said top open end, said inside annular flange having a tapered inner diameter, said plug has a plug base for press-fitting into the tapered inner diameter of said inside annular flange tightly to seal the passage of said top open end, a split coupling bolt axially forwardly extended from a bottom end of said plug base and slidably coupled to said inside annular flange, a shoulder located on a top end of said plug base for stopping outside said top open end of said tubular container, and a head formed integrally with a top side of said shoulder opposite to said plug base.

2. The fluid applicator as claimed in claim 1, wherein said floating stopper is prepared from a liquid material having a high molecular weight that is stable under room temperature.

3. The fluid applicator as claimed in claim 1, wherein said head of said plug has the shape of a cartoon figure.

4. The fluid applicator as claimed in claim 1, wherein said plug base has a chamfered bottom edge to facilitate insertion of said plug base into said tapered inner diameter of said inside annular flange of said tubular container.

5. The fluid applicator as claimed in claim 1, wherein said plug has a blind hole axially extending through said plug base, said split coupling bolt and said shoulder into the inside of said head.

6. The fluid applicator as claimed in claim 1, further comprising an absorptive applicator tip fastened to said bottom open end of said tubular container and adapted for absorbing said fluid for application.

7. The fluid applicator as claimed in claim 1, wherein said fluid is a perfume.

8. The fluid applicator as claimed in claim 1, wherein said fluid is a medicine.

9. A fluid applicator, comprising:
    a tubular container having a top open end and a bottom open end opposite to said top open end;
    a floating stopper mounted in said tubular container and adapted to seal said bottom open end;
    a fluid filled in said tubular container in between said top open end and said bottom open end; and
    a plug for closing the top open end of said tubular container; and
    wherein when said plug is opened from said top open end of said tubular container for allowing the atmospheric pressure to enter said top open end, said floating stopper is forced to adhere to the peripheral wall of said tubular container for allowing said fluid to flow out of said bottom open end; when said plug seals said top open end of said tubular container, the atmospheric pressure is prohibited from entering said top open end, and said floating stopper stops said bottom open end again, said tubular container has an inside annular flange located on said top open end, said inside annular flange having a tapered inner diameter, said plug has a plug base for press-fitting into the tapered inner diameter of said inside annular flange tightly to seal the passage of said top open end, a stub rod axially forwardly extended from a bottom end of said plug base and insertable through the tapered inner diameter of said inside annular flange, a shoulder located on a top end of said plug base for stopping outside said top open end of said tubular container, and a head formed integrally with a top side of said shoulder opposite to said plug base.

10. The fluid applicator as claimed in claim 9, wherein said floating stopper is prepared from a liquid material having a high molecular weight that is stable under room temperature.

11. The fluid applicator as claimed in claim 9, wherein said head of said plug has the shape of a cartoon figure.

12. The fluid applicator as claimed in claim 9, wherein said plug base has a chamfered bottom edge to facilitate insertion of said plug base into said tapered inner diameter of said inside annular flange of said tubular container.

13. The fluid applicator as claimed in claim 9, wherein said plug has a blind hole axially extending through said plug base, said stub rod and said shoulder into the inside of said head.

14. The fluid applicator as claimed in claim 9, further comprising an absorptive applicator tip fastened to said bottom open end of said tubular container and adapted for absorbing said fluid for application.

15. The fluid applicator as claimed in claim 9, wherein said fluid is a perfume.

16. The fluid applicator as claimed in claim 9, wherein said fluid is a medicine.

* * * * *